United States Patent [19]

Adekunle et al.

[11] Patent Number: 5,178,879
[45] Date of Patent: Jan. 12, 1993

[54] CAPSAICIN GEL

[76] Inventors: Michael Adekunle, 1660 N. Prospect Ave., #705, Milwaukee, Wis. 53202; James J. Flowers, 10917 N. San Marino Dr., Mequon, Wis. 53092

[21] Appl. No.: 870,510

[22] Filed: Apr. 17, 1992

[51] Int. Cl.$^5$ ...................... A61K 9/06; A61K 35/78
[52] U.S. Cl. .................. 424/484; 424/195.1; 514/627; 514/783; 514/817; 514/944
[58] Field of Search ............ 424/401, 78.05; 514/944, 817

[56] References Cited

U.S. PATENT DOCUMENTS

| | | | |
|---|---|---|---|
| 4,313,958 | 2/1982 | LaHann | 424/324 |
| 4,486,450 | 12/1984 | Bernstein | 424/324 |
| 4,525,347 | 6/1985 | Inagi | 424/78.05 |
| 4,533,546 | 8/1985 | Kishi | 424/78.05 |
| 4,536,404 | 8/1985 | Bernstein | 514/627 |
| 4,543,251 | 9/1985 | Kamishita | 424/78.05 |
| 4,546,112 | 10/1985 | LaHann et al. | 514/627 |
| 4,702,916 | 10/1987 | Geria | 514/944 |
| 4,874,605 | 10/1989 | Urban | 514/944 |
| 4,997,853 | 3/1991 | Bernstein | 514/626 |

*Primary Examiner*—Thurman K. Page
*Assistant Examiner*—Sally Gardner
*Attorney, Agent, or Firm*—Quarles & Brady

[57] ABSTRACT

Clear, water-washable, non-greasy gels useful for topical pain relief contain capsaicin, water, alcohol and a carboxypoly-methylene emulsifier. A method of preparing the gels is disclosed.

4 Claims, No Drawings

CAPSAICIN GEL

FIELD OF THE INVENTION

The present application relates to pharmaceutical compositions. More particularly, it relates to gels containing capsaicin.

BACKGROUND OF THE INVENTION

Many over the counter (o-t-c) products used to relieve deep seated pain by topical application contain irritants and relieve pain by a counterirritant action rather than by a direct analgesic effect. When such irritant containing products are applied locally to the intact skin in proper concentration to induce hyperemia and redness without blistering, they result in a feeling of warmth which may be followed by relief of pain.

Irritants have been used most successfully in treating neuralgias, rheumatoid arthritis, bursitis, myositis and integumental pain.

Capsicum is an oleoresin obtained by extracting cayenne pepper with ether. It and its active ingredient, capsaicin, have been used for many years as irritants in o-t-c compositions intended for pain relief including such well known lotions as HEET, OMEGA OIL and SLOAN'S LINIMENT. In addition, the topical analgesic cream ZOSTRIX (supplied by Gen Derm Corporation of Northbrook, Illinois) contains capsaicin 0.025% w/w in a petrolatum containing cream.

The currently available products containing capsicum or capsaicin are useful and acceptable for many purposes. However, there are applications in which it would be advantageous to have a clear, water-washable, non-greasy, capsaicin containing gel, and no such gels are currently available.

SUMMARY OF THE PRESENT INVENTION

It is an object of the present invention to disclose clear, water-washable, non-greasy gels containing capsaicin and a method of making such gels.

The gels of the present invention are clear, water-washable, non-greasy gels which consist essentially of capsaicin, alcohol, water, and an effective amount of carboxypolymethylene emulsifying agent to form a gel with the water and the alcohol. The gel also may contain a neutralizing agent for the carboxypolymethylene, a sequestering agent and preservatives and stabilizers.

The preferred gel contains by weight about 0.025% to about 0.075% of capsaicin; about 0.5% to about 2% of a carboxypolymethylene; about 30% to about 45% of ethyl alcohol and about 55% to about 70% of water. The preferred gel is clear, water-washable, cool to the touch, non-greasy, and it has spread-ability. It also differs from prior art capsaicin containing creams and ointments because it contains the capsaicin in solution as opposed to in suspension and it contains no oil or petroleum.

The method of preparing the gels of the present invention comprises dissolving the capsaicin in alcohol, adding the carboxypolymethylene to form a dispersion and then adding the water and blending the mixture to form the gel.

The foregoing and other objects and advantages of the gels of the present invention will be apparent to those skilled in the art from the description which follows:

DESCRIPTION OF THE PREFERRED EMBODIMENTS

The preferred gels have the following formula:

| | |
|---|---|
| Capsaicin | 0.025% to 0.075% |
| Carbopol 1342 or 1382 (carboxypolymethylene) | 1.000% |
| Neutrol TE (tetrahydroxypropyl ethylenediamine) | 1.500% |
| Polysorbate 20 (polyoxyethylene (20) sorbitan monolaurate) | 0.200% |
| Uvinol MS 40 (2-hydroxy-4-methoxy-benzophenone-5-sulfonic acid) | 0.010% |
| Germall II (diazolidinyl urea) | 0.300% |
| Di Sodium EDTA USP | 0.020% |
| Ethyl Alcohol SDA 40 | 38.000% |
| Distilled or Ion Exchange Purified Water q. ad. | 100.000% |

The preferred gels are made adding the capsaicin to the ethyl alcohol and mixing until it dissolved, adding to the resulting solution, the Uvinul MS 40, and the Carbopol and mixing until they are evenly dispersed. To the resulting dispersion 90% of the purified water is added and then mixed. The Di sodium EDTA is then added with mixing until a uniform dispersion is formed. The Polysorbate 20, Germall II and Neutrol TE are dissolved in the remainder of the water. The resulting aqueous solution is then added to the previously prepared uniform dispersion and the two blended to form a gel.

The preferred gel containing 0.025% capsaicin has the following formula:

| | |
|---|---|
| Capsaicin | 0.025% |
| Carbopol 1342 or 1382 | 1.000% |
| Neutrol TE | 1.500% |
| Polysorbate 20 | 0.200% |
| Uvinul MS 40 | 0.010% |
| Germall II | 0.300% |
| Di Sodium EDTA USP | 0.020% |
| Ethyl Alcohol SDA 40 | 38.000% |
| Purified Water | 58.945% |

The gels containing the higher concentrations of the capsaicin contain the same percentages of ingredients as the 0.025% gel except that they contain proportionately less water.

The capsaicin used in the preferred formulations is synthetic capsaicin which is the chemical, trans-8-methyl-N-vanillyl-6-nonenamide. It is available from Penta Manufacturing of Fairfield, N.J.

The carboxypolymethylene is an emulsifying agent available from B.F. Goodrich, Specialty & Polymers & Chemicals Division, Cleveland, Ohio under the product name CARBOPOL. Both CARBOPOL 1342 and CARBOPOL 1382 can be used. The carboxypolymethylene is a vinyl polymer with active carboxyl groups. It is described by the manufacturer as being a hydrophobically modified, cross-linked acrylic acid polymer manufactured by a co-solvent manufacturing technique using a blend of ethyl acetate and cyclohexane solvents.

The tetrahydroxypropyl ethylenediamine is used to neutralize the acidic carboxyl groups of the carboxypolymethylene. It is available as NEUTROL TE from BASF Corporation of Parsippany, N.J.

The polyoxymethylene (20) sorbitan monolaurate is a surfactant available from ICI Americas Inc. of Wilmington, Del. under the product name POLYSORBATE 20 (TWEEN).

The 2-hydroxy-4-methoxybenzophenone-5-sulfonic acid is an ultraviolet stabilizer. It is available as Uvinul MS 40 from BASF Corporation.

The diazolidinyl urea is an antimicrobial preservative. It is available as Germall II from Sulton Laboratories, Inc. of Chatham, N.J.

The Di Sodium EDTA is a sequestering agent. It is available commercially from many sources.

The ethyl alcohol referred for use in the gel formulation is Ethyl Alcohol SDA 40-2 which is a 190 proof denatured alcohol available from Quantum of Cincinnati, Ohio. It contains small amounts of water, t-butyl alcohol and less than 0.1% of prucine sulfate.

In clinical tests the gels of the present invention were preferred by patients and doctors over the commercially available creams. The gels were easy to spread and water-washable. In addition, they appeared to be more effective than creams containing the same concentration of capsaicin.

It will be apparent to those skilled in the art that a number of changes and modifications can be made without departing from the spirit and scope of the present invention. Therefore, it is intended that the invention only be limited by the claims.

We claim:

1. A clear, water-soluble, non-greasy gel consisting essentially of the following by weight:
   (a) about 0.025% to about 0.075% capsaicin;
   (b) about 0.5% to about 2% of a carboxypolymethylene emulsifying agent;
   (c) about 30% to about 45% ethyl alcohol; and
   (d) about 55% to about 70% water.

2. A clear, water-soluble, non-greasy gel consisting essentially of the following by weight:
   (a) about 0.025% to about 0.075% capsaicin;
   (b) about 1% of a carboxypolymethylene emulsifying agent;
   (c) about 1.5% of tetralhydroxypropyl ethylenediemine as a neutralizing agent for the carboxypolymethylene;
   (d) about 0.20% of disodium EDTA as a sequestering agent;
   (e) about 0.30% of diazolidinyl urea as an antimicrobial preservative;
   (f) about 0.20% of a surfactant;
   (g) about 38% ethyl alcohol; and
   (h) about 59% water.

3. A gel of claim 2 which also contains an effective amount of an ultraviolet stabilizer.

4. A method of preparing a clear, water-soluble, non-greasy capsaicin gel of claim 2 which comprises forming a first solution by dissolving the capsaicin in the ethyl alcohol, dispersing the carboxypolymethylene emulsifying agent in the capsaicin/ethyl alcohol, and adding about 90% of the water and the sequestering agent; preparing a second solution containing the neutralizing agent, the antimicrobial agent, the surfactant and the remainder of the water; and, combining the first solution and the second solution to form a gel.

* * * * *